US010837068B2

United States Patent
Cai et al.

(10) Patent No.: US 10,837,068 B2
(45) Date of Patent: Nov. 17, 2020

(54) RICE MITOCHONDRIAL STERILE GENE AND APPLICATION THEREOF

(71) Applicants: Jiangxi Super-rice Research and Development Center, Nanchang (CN); Nanchang University, Nanchang (CN)

(72) Inventors: Yaohui Cai, Nanchang (CN); Hongwei Xie, Nanchang (CN); Xiaojue Peng, Nanchang (CN); Mingjuan Qian, Nanchang (CN); Yicong Cai, Nanchang (CN); Xia Ding, Nanchang (CN); Youlin Zhu, Nanchang (CN); Long'An Yan, Nanchang (CN)

(73) Assignees: Jiangxi Super-rice Research and Development Center, Nanchang (CN); Nanchang University, Nanchang (CN)

( * ) Notice: Subject to any disclaimer, the term of this patent is extended or adjusted under 35 U.S.C. 154(b) by 35 days.

(21) Appl. No.: 15/876,805

(22) Filed: Jan. 22, 2018

(65) Prior Publication Data

US 2018/0208941 A1    Jul. 26, 2018

(30) Foreign Application Priority Data

Jan. 20, 2017    (CN) .......................... 2017 1 0048088

(51) Int. Cl.
| | | |
|---|---|---|
| *C12Q 1/68* | (2018.01) | |
| *C12Q 1/6895* | (2018.01) | |
| *C12N 15/82* | (2006.01) | |
| *C07K 14/415* | (2006.01) | |

(52) U.S. Cl.
CPC .......... *C12Q 1/6895* (2013.01); *C07K 14/415* (2013.01); *C12N 15/8205* (2013.01); *C12N 15/8289* (2013.01); *C12Q 2600/13* (2013.01)

(58) Field of Classification Search
None
See application file for complete search history.

(56) References Cited

PUBLICATIONS

Emery et al (2003, "Radial Patterning of *Arabidopsis* Shoots by Class III HD-ZIP and KANADI Genes", Current Biology 13:1768-1774).*
Merriam Webster Online Dictionary. 2005, www.m-w.com/home.html.*

* cited by examiner

*Primary Examiner* — Stuart F Baum
(74) *Attorney, Agent, or Firm* — Lucas & Mercanti, LLP (57) ABSTRACT

Provided is a rice mitochondrial sterile gene and the application thereof. A rice mitochondrial sterile gene and a coding sequence thereof are disclosed. A specific molecular marker was designed from said gene sequence and enables a rapid and effective screening and identification of D1-type cytoplasm from wild rice for breeding a new D1-type cytoplasm sterile line. A specific sequence in the mitochondria genome of D1-type cytoplasm sterile line was identified by comparative genomics. Sterility-related ORFs were identified from gene prediction and expression difference analysis. A plant transformation vector was constructed to transform maintainer line for verification and sterile function.

3 Claims, 4 Drawing Sheets

Specification includes a Sequence Listing.

RICE MITOCHONDRIAL STERILE GENE AND APPLICATION THEREOF

CROSS-REFERENCE TO RELATED APPLICATIONS

This application claims the priority of Chinese Patent Application No. 201710048088.8 filed Jan. 20, 2017, the contents of which are incorporated herein by reference.

TECHNICAL FIELD

The invention relates to the field of rice breeding, and particularly to a sterile gene of rice mitochondria and the application thereof.

BACKGROUND ART

In 1970s, it was a success of applying "three-line method" to breed a hybrid rice in China. Due to extensive planting of such hybrid rice for production in large area, a second huge leap in rice yield per unit area was achieved in China. From 1975 to 2005, the total planting area of hybrid rice was 5.25 billion mu, with 650 million tons of unhusked rice harvested. Therefore, the development of hybrid rice is an important route for improving the yield of crops and for solving the safety problem of crops (Longping Yuan, 2008). The basis for three-line hybrid rice is cytoplasmic male sterility. Since the discovery and application of the wild abortive (WA) type cytoplasmic male sterile line in large area, breeding experts have bred more than 60 types of cytoplasmic sources that were derived from WA type, Yunnan Dian type (Dian I and Dian II), HL type, Gang type, K type and Maxie type, etc. Although there are large differences in cytoplasmic source and sterility characteristics, the rice can be classified into two types: sporophytic sterile type and gametophytic sterile type (Yingguo Zhu, 2000). While Yunnan Dian type, BT type and HL type are gametophytic sterile line; WA type, D type, K type and Gang type are sporophytic sterile type. Most of the gametophytic sterile lines have the same restorer and maintainer relationship, and most of the sporophytic sterile types have the same restorer and maintainer relationship, but the gametophytic sterile lines and the sporophytic sterile lines have the inverse restorer and maintainer relationship.

Among the gametophytic cytoplasmic male sterile lines, the BT-type cytoplasmic male sterile gene orf79 and the HL-type cytoplasmic male sterile gene orfH79 have been cloned. Due to allelic variations, there is 97% sequence homology between the two sterile genes (Wang et al. 2006; Peng et al. 2010). The orf79 allelic variation gene was also identified in Dian-type sterile line. With regard to the sporophytic-type cytoplasmic male sterile lines, Luo et al identified a WA-type sterile gene WA352 by using a whole mitochondrial genome expression analysis. The gene was comprised of 3 mitochondrial genome fragments and one fragment of unknown source. Other sporophytic cytoplasmic sterile types such as Yinshui type, Dwarf type (Aibai type in Chinese), Gang type, Java type, Maxie type and K type all contain sterile gene WA352 (Luo et al. 2013).

At present, the main cytoplasmic male sterile types recognized globally are WA, HL and BT, in which the former two types of sterile cytoplasm are derived from wild rice. In 1970s, breeding experts from both China and overseas also used wild rice to have bred other 13 cytoplasmic types for the cytoplasmic donor, such as Yacheng wild rice cytoplasm, Tiandu wild rice cytoplasm (Yingguo Zhu, 2000). Therefore, excavating cytoplasm from wild rice is one important route for breeding new types of cytoplasmic male sterile lines. Dongxiang wild rice is a perennial wild rice, and is the northernmost wild rice variety in the world to date. It is entitled "wild-type plant of panda" in China and overseas (Yinan Huang et al, 2012). In 1980s, Dongxiang wild rice has been used as a cytoplasmic donor by Rice Department of Jiangxi Academy of Agricultural Sciences to breed a sterile line called Guojiyouzhan A; however, it was not widely applied and used because the restoration source that could restore the fertility of the new sterile line was not found. In recent years, a new cytoplasmic male sterile line D1A has been bred by Jiangxi Super Rice Research and Development Center that used Dongxiang wild rice as a cytoplasmic donor. The D1A was then used as a cytoplasmic source to back-cross with Peiai 64, Tianfeng B, K17B, Xieqingzao B, II-32B, 2454B, Yue 4B, 9311 and the like, respectively, to obtain a new batch of this kind of CMS lines. Said type of sterile line is a sporophytic sterile line, and it has been identified in the molecular marker that said sterile line does not include sporophytic sterile gene WA352 that has been cloned. There is no pollen abortion; the abortion is complete; and the sterility is very easy to be stabilized. The maintainer line spectrum is broad, and a majority of the cultivated species can be its maintainer line. Also, a restorer line was found in Chinese wild rice, to achieve a cultivated rice trans-breeding that restores gene by the restorer line of wild rice, with a maximal restoration rate of 85.1%. By using such restorer resource, we are also screening for an outstanding restoration line and prepare hybrid F1. Thus, its sterility characteristics, molecular mechanism, as well as restorer and maintainer relationship is completely different from other sterile lines that are currently promoted. It is a new sporophytic sterile type named D1 type. The research and application of such sterile line as a complementary type significantly increases the abundance of types of hybrid rice, and has an important value in promoting a sustained development of hybrid rice.

However, the clones of the D1 cytoplasmic sterile gene have not been obtained yet. Cloning the D1-type sterile gene is important for understanding the mechanism of pollen-free type cytoplasmic male sterility, for creating new D1-type cytoplasmic male sterile line and restorer line, for breeding D1-type hybrid rice species, and for improving the yield of rice by leveraging the advantages of hybrid rice.

In view of the above, the present disclosure is thus proposed.

DISCLOSURE OF THE INVENTION

The present disclosure provides a rice mitochondrial sterile gene and a coding sequence thereof. A specific molecular marker was designed from said gene sequence. The molecular marker can rapidly and effectively screen and identify D1-type cytoplasm from wild rice, for breeding new D1-type cytoplasmic sterile line. A specific sequence in the mitochondria genome of D1-type cytoplasm sterile line was identified by comparative genomics. Sterility-related ORFs were identified from genetic prediction and expression difference analysis. A plant transformation vector was constructed to transform a maintainer line for verification function and sterile function.

In order to achieve the objective above, the embodiments below were employed.

A rice mitochondrial sterile gene, characterized in that the gene includes a sequence selected from a group consisting of:

a) a nucleotide sequence having SEQ ID NO: 1;

b) a nucleotide sequence that is capable of hybridizing to the nucleotide sequence defined in a) under a stringent condition; and c) a nucleotide sequence that is complementary to the nucleotide sequence in a) or b).

In recent years, a new type CMS line D1A has been bred by Jiangxi Academy of Agricultural Sciences that used Dongxiang wild rice as a cytoplasmic donor. Said sterile line type is a sporophytic sterile line. There is no pollen abortion; the abortion is complete; and the fertility is quite easy to be stabilized. The sterile line is named D1-type cytoplasm. It has been identified in the molecular marker that said sterile line does not include sporophytic sterile gene WA352 that has been cloned. The present applicant identified a D1-type specific open reading frame (ORF) in the mitochondrial genome of D1-type sterile line by mitochondria sequencing and comparative genomics. Said open reading frame encodes 182 amino acids, and the sequence thereof is represented by SEQ ID NO: 1, and it can cause cytoplasmic male sterility.

As will be understood by those skilled in the art, the rice mitochondrial sterile gene of the present disclosure also includes a highly-homologous functionally equivalent sequence that is highly homologous to SEQ ID NO: 1 and possesses a similar sterility regulation function.

The highly-homologous functionally equivalent sequence includes a DNA sequence that is capable of hybridizing to the DNA of sequence represented by SEQ ID NO: 1 under a stringent condition. The "stringent condition" as used by the present disclosure is commonly known, including, for example, hybridizing in a hybridization solution containing 400 mM NaCl, 40 mM PIPES (pH6.4) and 1 mM EDTA for 12-16 hours at 60° C., followed by washing in a washing solution containing 0.1% SDS and 0.1% SSC for 15-60 minutes at 65° C.

The functionally equivalent sequence also includes a sequence that is at least 90%, 95%, 96%, 97%, 98% or 99% identical to the sequence represented by SEQ ID NO: 1; the sequence has a gene sequence of sterility regulation function and can be isolated from any plants. Here, the percentage of sequence identicalness can be obtained by commonly known algorithm in bioinformatics, which includes Myers and Miller algorithms (Bioinformatics, 4(1): 11-17, 1988), Needleman-Wunsch global comparison method (J. Mol. Biol., 48(3): 443-53, 1970), Smith-waterman local comparison method (J. Mol. Biol., 147: 195-197, 1981), Pearson and Lipman similarity search method (PNAS, 85(8): 2444-2448, 1988), and Karlin and Altschul algorithm (Altschul et al, J. Mol. Biol., 215(3): 403-410, 1990; PNAS, 90: 5873-5877, 1993). These are well-known to those skilled in the art.

An expression vector containing a rice mitochondrial sterile gene, characterized in that the gene comprises a sequence selected from the group consisting of:

a) a nucleotide sequence comprising SEQ ID NO: 1;

b) a nucleotide sequence capable of hybridizing to the nucleotide sequence defined in a) under a stringent condition; and c) a nucleotide sequence that is complementary to the nucleotide sequence defined in a) or b).

Preferably, the expression vector is a PCAMBIA1301 vector.

An engineered microorganism that is transformed by the expression vector described above.

Preferably, the engineered microorganism is an *Agrobacterium*.

The gene as provided by the present disclosure can be inserted into plasmid, cosmid, yeast artificial chromosome (YAC), bacterial artificial chromosome (BAC) or any other vectors that are suitable for being transformed into a host cell. The host cell is preferably a bacterial cell, particularly a bacterial cell for cloning or storing polynucleotide, or for transforming plant cells; the bacterial cells are, for example, *Escherichia coli* (*E. coli*), *Agrobacterium*, *Agrobacterium tumefaciens* (*A. tumefaciens*) or *Agrobacterium rhizogenes* (*A. rhizogenes*); and most preferably, *Agrobacterium*.

Before describing the compound, the composition, the protein, the peptide and the method of the present disclosure, it should be understood that these embodiments are not limited to specific methods, embodiments and reagents as described, as they can be varied. It should also be understood that the terminologies used herein are only for the purpose of describing specific embodiments, and are not intended to limit the scope of the present embodiments or claims.

When the host cell is a plant cell, the expression cassette or vector containing the gene provided by the present disclosure can be inserted into the genome of the transformed plant cells. The insertion can be site-specific or random insertion. Preferably, the insertion can be achieved by homologous recombination. In another aspect, the expression cassette or vector can be kept outside of the chromosome. The expression cassette or vector of the present disclosure can be present in nucleus, chloroplast, mitochondria and/or plastid of the plant cell. Most preferably, the expression cassette or vector containing the gene or DNA sequence provided by the present disclosure is inserted into the mitochondrial DNA of the plant.

An amino acid sequence encoded by the gene described above.

It is well known to those skilled in the art about how to convert the gene sequence provided by the present disclosure to amino acid sequence.

Preferably, the amino acid sequence described above is represented by SEQ ID NO: 2.

The amino acid sequence of SEQ ID NO: 2 is obtained by expression of the nucleotide sequence of SEQ ID NO: 1.

A primer pair, in which the upstream primer and the downstream primer are represented by SEQ ID NO: 3 and SEQ ID NO: 4, respectively.

The primer pair is designed based on the gene of SEQ ID NO: 1.

Use of the gene and the primer pair described above for identification and/or assistance in breeding of a D1-type rice sterile line and of a corresponding restorer line thereof.

A method of identifying a rice containing a D1-type cytoplasmic sterile gene, the method including steps of:

amplifying a genomic DNA of a rice to be tested by the primer pair described above;

identifying the amplified product by electrophoresis; if the product comprises a band of 549 bp, the rice sample to be tested is indicated to contain the D1-type cytoplasmic sterile gene.

Preferably, in the method of identifying a rice comprising D1-type cytoplasmic sterile gene as described above, the Tm is 50° C. and the reaction cycle is 28 during the reaction process of the amplification.

The present disclosure further provides a transgenic method, or a method of producing a plant; the method including:

(1) constructing an expression vector provided by the present disclosure;

(2) introducing the expression vector obtained from step (1) into a plant cell; or introducing the expression vector into a plant cell via mediation of an intermediate host cell such as *Agrobacterium* or the like;

(3) reproducing a transgenic plant;

(4) selecting a transgenic plant; and (5) optionally, proliferating the plant obtained from step (4) to generate progenies.

The transgenic plant of the present disclosure is prepared by using transformation method known to those skilled in the art of plant biotechnology. Any method can be used for transforming the recombined expression vector into the plant cell to produce the transgenic plant of the present disclosure. The transformation method can include direct or indirect transformation method. A suitable direct method includes polyethylene glycol (PEG) induced DNA intake, liposome-mediated transformation, introduction by a gene gun, electroporation, microinjection or the like. In the detailed description of the present disclosure, an *Agrobacterium* based transformation technology is employed by the present disclosure. The *Agrobacterium* can include plasmid (e.g. conventional plasmid such as Ti or Ri plasmid; PCAMBIA1301 is preferably used by the present disclosure) and DNA element of the present disclosure (i.e. the gene or DNA sequence as described above). The plasmid and the element are firstly transfected into the *Agrobacterium* before being transformed to the plant, and the DNA element will be integrated into the genome of the plant cell; and more specifically, the DNA element will be integrated into the genome of the mitochondria. The nucleotide sequence of the present disclosure is particularly suitable for a plant cell of rice, but this does not exclude the possibility of also possessing sterility regulation function in other species.

BRIEF DESCRIPTION OF DRAWINGS

In order to clarify the specific embodiments of the present disclosure and the embodiment in the prior art, the drawings used in the description of the specific embodiments or in the prior art will be briefly introduced below. Apparently, the drawings described below are merely part of the embodiments of the present disclosure. In the absence of creative effort, those of ordinary skill in the art can obtain other figures based on these drawings.

DETAILED DESCRIPTION OF EMBODIMENTS

Unless otherwise stated, all of the technologies and scientific terminologies used in the present disclosure have the same meaning as those commonly understood by those of ordinary skill in the art of the present embodiments. Although the methods and materials that are similar or equivalent to the method and material described in the present disclosure can be employed in the practice or test of the present embodiment, suitable method and material are still described below. All of the publications, patent applications, patent documents and other literatures as mentioned in the present disclosure are incorporated herein by reference. In the case of conflict, the present specification (including definition) will predominate. In addition, the materials, methods and examples are merely illustrative but not limiting. Other characteristics and advantages of the embodiments will become apparent from the detailed description and claims below.

In order to facilitate the understanding of embodiments described herein, some embodiments will be referred to and described in specific languages. The terminologies used herein are merely for the purpose of describing the detailed embodiments, but not intend to limit the scope of the present disclosure.

The embodiments of the present disclosure will be described in detail below in combination with examples. However, it will be appreciated by those of skill in the art that the examples below are merely for illustrating the present disclosure, and should not be construed as limiting the scope of the present disclosure. If a condition is not indicated in the example, it is to be carried out based on the conventional condition or a condition suggested by the manufacturer. If the manufacturers of any reagents or equipment are not indicated, the reagents or equipment are conventional products that are commercially available.

The present disclosure provides a D1-type sterile gene orf182 and the coding sequence thereof. A specific molecular marker was designed from said gene sequence. The molecular marker can rapidly and effectively screen and identify D1-type cytoplasm from wild rice for breeding a new D1-type cytoplasmic sterile line. A specific sequence in the mitochondria genome of D1-type cytoplasm sterile line was identified by comparative genomics. Sterility-related ORFs were identified from genetic prediction and expression difference analysis. A plant transformation vector was constructed to transform a maintainer line for verification function and sterile function.

In order to achieve the objective above, the following technical measures were taken by the present disclosure:

(A) Screening for Sterile Candidate Gene Orf182

Figure 1:
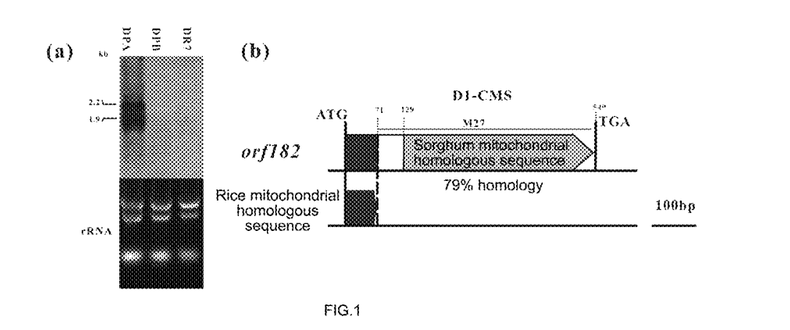
FIG. 1 shows a structure of a sterile candidate gene orf182 and comparative expression analysis; (a) Northern Blot: hybridization comparison of expression pattern among D1-CMS DPA, maintainer line DPB and homogenous restorer line DR7 in young panicles; (b) orf182 gene structure, in which the white square portion represents a sequence region of unknown source.
Figure 2:
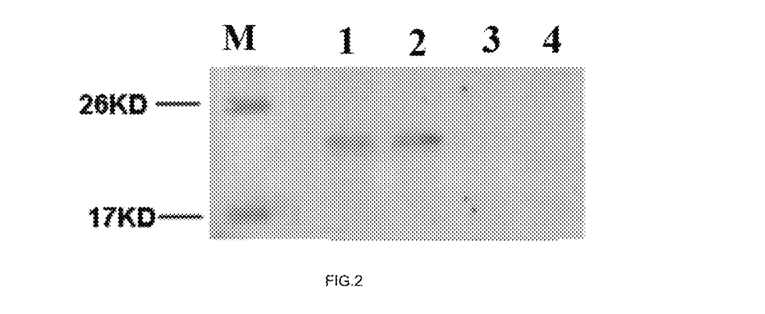
FIG. 2 shows a Western blot which detects the expression of ORF182 in D1-type sterile line and maintainer line; Lane 1 and Lane 3 are total proteins of the young panicles of the D1-type sterile line DPA and the maintainer line DPB, respectively. Lane 2 and Lane 4 are total proteins of the etiolated seedling of the D1-type sterile line DPA and the maintainer line DPB.
Figure 3:
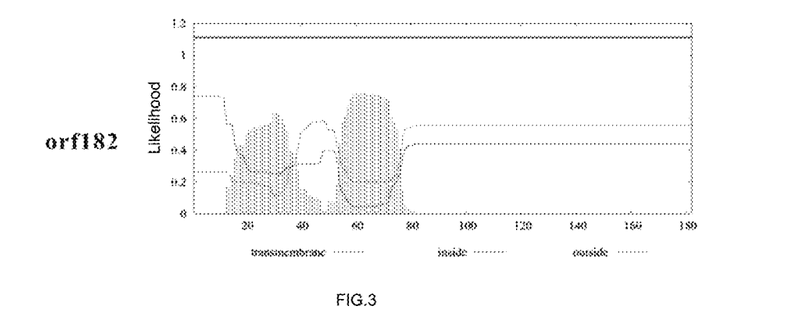
FIG. 3 shows a structure of transgenic fragment.

D1-CMS mitochondrial specific sequence was screened by a comparative analysis of D1-CMS DPA mitochondrial genome with rice mitochondrial genome of WA-CMS, LD-CMS, CW-CMS, N, Nipponbare, RT98C, respectively. 3 sequences that were completely specific to D1-CMS were screened by comparative analysis. By using the specific sequence as a probe and using Northern blot hybridization to detect expression pattern in the DPA, DPB and homogeneous restorer line DR7 young panicles, it was found that two transcripts of a size of 2.6 kb and 1.9 kb were detected, respectively, in mitochondrial specific sequence M27 and DPA, but little hybridization signals were detected in DPB and DR7. The M27 sequence was subsequently analyzed, and an open reading frame (ORFs) was detected, which encodes 182 amino acids. Said ORF was composed of 3 portions: one portion is a rice mitochondrial sequence fragment, another portion is an unknown sequence, and the largest portion of sequence is a sequence which is 79% homologous to sorghum mitochondrial sequence (FIG. 1). At present, the cloning of a plant male sterile gene normally include a mitochondrial functional gene sequence or a mitochondrial open reading frame sequence that has been identified to have unknown function, but orf182 neither contain any mitochondrial functional gene sequence nor any open reading frame sequence. In order to verify whether orf182 is capable of being translated into a functional protein, a monoclonal antibody against ORF182 was firstly prepared commercially, and mitochondrial total proteins of young panicles and etiolated seedling of DPA and DPB were extracted, respectively. The Western blot result suggested that ORF182 protein was only enriched in DPA mitochondria, in which a band of around 20 kD was detected; on the other hand, a hybridization signal was neither detected in the young panicles nor in the etiolated seedling of DPB (FIG. 2). Different from the current rice mitochondrial sterile genes cloned (in which WA352 containing 3 trans-membrane domains; ORF79 and ORFH79 both containing 1 trans-membrane domain), no trans-membrane domain was found in ORF182 according to the prediction of mitochondria trans-membrane domain prediction software TMHMM (http://www.cbs.dtu.dk/services/TMHMM). Therefore, orf182 is a new CMS candidate gene, and its nucleotide sequence is represented by SEQ ID NO: 1.

(B) Verification of Transgenic Sterile Candidate Gene Orf182

Figure 4:
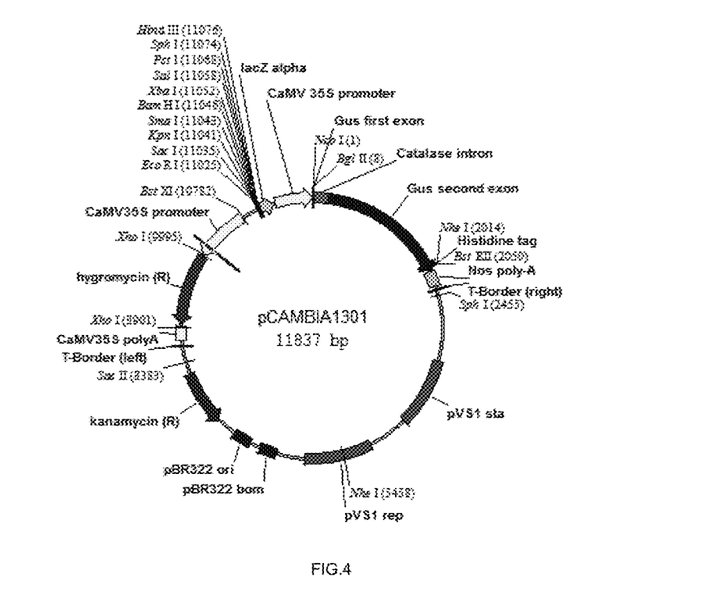
FIG. 4 shows a vector of PCAMBIA1301.
Figure 5:
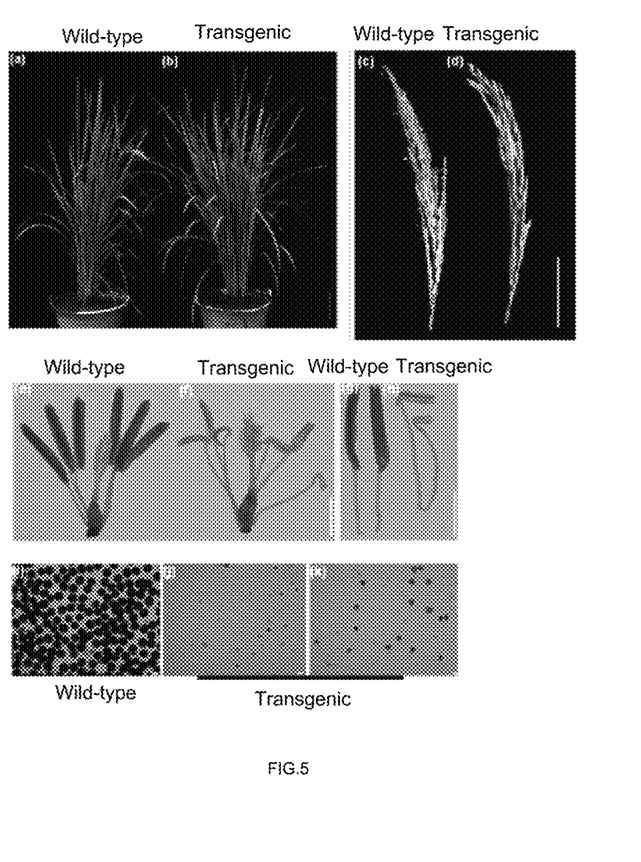
FIG. 5 shows the impact of orf182 on the transgenic rice types and sterility; (a) and (b) showed a morphology of plants for wild-type plants and transgenic plants, the scale bar=10 cm; (c) and (d) showed a phenotype of tassels for wild and transgenic plants, respectively, at the time of blossom, the scale bar=5 mm; (e) and (g), (f) and (h) showed a morphology of anther for wild-type and transgenic plant, respectively, during a heading period, the scale bar=2 mm; (i) showed a staining microscopy of wild-type pollen I2-KI, (j) and (k) showed a staining microscopy of transgenic pollen I2-KI, the scale bar=30 μm.
Figure 6:
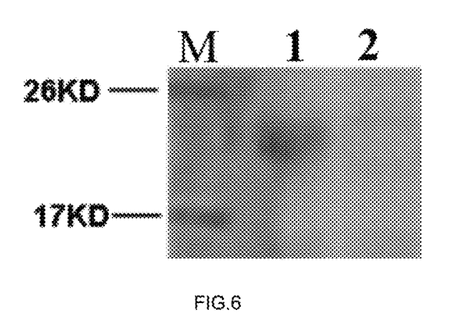
FIG. 6 shows a Western blot which analyzed the expression of transgenic plant proteins. Lane 1 and 2 are total proteins of young panicles of the transgenic plants.
Figure 7:
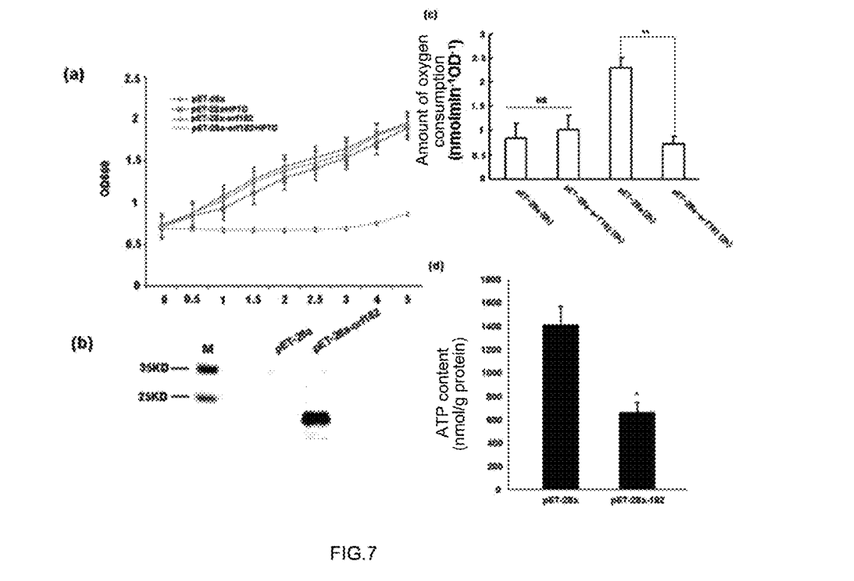
FIG. 7 showed a toxicity test of ORF182 in *E. coli*. (a) growth curve of orf182 transgenic *E. coli* in liquid culture medium in the presence or absence of IPTG induction, and *E. coli* transfected with empty vector pET-28a serves as a control; (b) Western blot which detects expression of orf182 in IPTG-induced transgenic *E. coli*; (c) detection of oxygen consumption in orf182-transfected *E. coli* and control after 2-hour culturing under IPTG induction at 37° C.; (d) detection of ATP content in orf182-transfected *E. coli* and control after 6-hour culturing under IPTG induction at 37° C.

In order to verify the function of orf182, a transgenic vector was constructed by using methods of PCR and gene synthesis. The sequence of the mitochondrial transit peptide of ATPγ derived from *Arabidopsis thaliana* (its nucleotide sequences is represented by SEQ ID NO: 5), was fused to the N-terminus of orf182, and the fused gene exhibited codon optimization according to the rice preferred genetic codons provided by the Kazusa DNA Research Institute http://www.kazusa.or.jp/codon/. The construct was then synthesized at the GenScript Biotech Corporation (China). Next, this sequence was digested with BamHI and ligated to the modified binary vector pCAMBIA1301, in which the CaMV 35S promoter was replaced by the strong constitutive promoter Pubi (the maize ubiquitin promoter), the entire expression cassette (Pubi::synthetic gene::Nos) (FIG. 4). Maintainer line Yuetai B was transformed through mediation of *Agrobacterium* and verified by PCR. A total of 12 positive seedlings of T0 generation were generated, among which 10 were completely pollen-free according to the pollen sterility detection, and the rest of the two seedlings contain small amount of typical sterile pollens. A BC1F1 population was obtained through back-cross of a pollen-free plant with a wild Yuetai B, and a pollen-free plant was also isolated from its progeny, which conforms to the 1:1 hereditary law of segregation. Total proteins of young panicles from the transgenic plant and the wild-type plant were extracted respectively, and the Western blot result indicated that ORF182 can be translated into a functional protein in transgenic rice (FIG. 7). Therefore, orf182 is a cytoplasmic male sterile gene.

(C) Action of ORF182 in Bacteria

The currently reported proteins encoded by sterility-related genes are all lethal to bacteria. In order to test the toxicity of ORF182 to bacteria, the coding sequence of orf182 was cloned into a bacterial expression vector PET28a, and *E. coli* was transformed. The Western blot detection indicated that ORF182 was expressed in the bacteria under the induction of IPTG. By comparing the result of growth curves in the presence or absence of IPTG induction, it was found that ORF182 significantly inhibited the bacterial growth. Also, we tested oxygen consumption by using oxygen electrode, and found a 52% reduction in respiratory rate in the bacteria containing orf182 gene.

(D) Amplification of Orf182 Gene in Other Cultivated Rice and Wild Rice

Specific primers were designed according to the orf182 gene:

Orf182F: represented by SEQ ID NO: 3;
Orf182R: represented by SEQ ID NO: 4;

The size of the amplification fragment is 549 bp. 520 cultivated rice and 446 wild rice species were detected by PCR amplification. The PCR program is as follows:

| | |
|---|---|
| (1) 94° C. | 5 min; |
| (2) 94° C. | 30 s; |
| (3) 50° C. | 30 s; |
| (4) 72° C. | 1 min; |
| (5) repeating steps (2), (3) and (4) for 28 cycles; | |
| (6) 72° C. | 10 min; |

TABLE 1 allelic variations of sterile gene orf182 from Chinese wild rice material

| Genotype | Frequency | Variation site of gene (bp) | | | | |
|---|---|---|---|---|---|---|
| | | 101 | 123 | 129 | 280 | 414 |
| A1 | 0.16 | G | C | A | G | A |
| A2 | 0.79 | A | A | G | A | G |
| A3 | 0.05 | G | A | A | G | A |
| coding difference | | GGA/ GAA | AGC/ AGA | CCA/ CCG | GAT/ AAT | GAA/ GAG |
| amino acid difference | | G/ E | S/ R | No | D/ N | No |

Note:
The frequency refers to a ratio of the number of wild rice containing the genotype to the total number of wild rice containing the orf182 gene.

The present applicant found that amplification of 520 cultivated rice species showed no band of said gene. The band of orf182 gene was only detected in 18 amplified Chinese ordinary wild rice species and 1 amplified Chinese weedy rice species. Sequencing was performed for the 19 materials containing the amplified orf182 gene, and a total of 5 SNPs sites were detected, among which 3 SNPs caused 3 variations in amino acids. Based on the types of variations of amino acids, it can be classified into 3 genotypes: A1, A2 and A3 (as shown in Table 1). Here, the source of A1 genotype is the same as DPA orf182, A2 has the highest frequency of distribution; whereas A3 has the lowest frequency of distribution. By cross-breeding the wild rice material and the cultivated rice containing the identified orf182 gene, it is possible to create new D1-type sterile line and the corresponding restorer line.

Lastly, it should be noted that the examples above are merely for illustrating the embodiments of the present disclosure, and should not be construed as a limitation thereto. Although the present disclosure has been illustrated in detail by referring to the examples above, it should be appreciated by those of ordinary skill in the art that modifications can be made to the described embodiments in the examples above, or alternatively, part or all of the technical features can be subjected to equivalent substitution. These modifications or substitutions will not cause the spirit of the corresponding embodiments to depart from the scope of embodiment in the examples of the to present disclosure.

The invention claimed is:

1. A primer pair, wherein an upstream primer and a downstream primer comprise SEQ ID NO: 3 and SEQ ID NO: 4, respectively.

2. A method of identifying a rice plant comprising a D1-type cytoplasmic sterile gene, wherein the method comprises the steps of:
amplifying a DNA fragment from genomic DNA of a rice plant to be tested using the primer pair of claim 1; and
identifying the amplified fragment by electrophoresis, wherein a rice plant producing a band of 549 bp indicates the rice plant comprises the D1-type cytoplasmic sterile gene.

3. The method of identifying a rice plant comprising a D1-type cytoplasmic sterile gene according to claim 2, wherein the melting temperature (Tm) of the PCR is 50° C. and the reaction cycle is 28.

* * * * *

SEQUENCE LISTING

```
<160> NUMBER OF SEQ ID NOS: 5

<210> SEQ ID NO 1
<211> LENGTH: 549
<212> TYPE: DNA
<213> ORGANISM: Oryza sativa

<400> SEQUENCE: 1
atgatgagat ttagttcaac ggataagaag gatagaagaa atatgctatt tgctgctatt      60
ccatctattt ggaaattcat ggacaacatt ttttttggtg gacctgggat gactatgcat     120
agcttaccac ttttcgtagt aaagaggctt gccgacactt gcgtgccagg cggcgctttc     180
ctgattgcac ttttgtgcag tctctcttcc acggcaatgg ccgctggtcc atccgactgg     240
atgcggggtg atccaaatga aacactccta cggcagaccg ataagcaaat agagaaggtc     300
aacgaggagt taaggaacgt gacatcccaa gccgtggaaa aagcgcagca gttccagttg     360
aacttgccgg gcacaagtga ggaacaaacg cacaccatcc gttctattct agaacatgat     420
cttgatggta tcgctctgaa tcaacgactt cgacgaatcc gaagatgggt caattctgga     480
gaaatcgaga atccggaaag cctattttgg cttcaaatta ttgaccaatt cagcaagtgg     540
ttcccatga                                                            549

<210> SEQ ID NO 2
<211> LENGTH: 182
<212> TYPE: PRT
<213> ORGANISM: Oryza sativa

<400> SEQUENCE: 2

Met Met Arg Phe Ser Ser Thr Asp Lys Lys Asp Arg Arg Asn Met Leu
1               5                   10                  15

Phe Ala Ala Ile Pro Ser Ile Trp Lys Phe Met Asp Asn Ile Phe Phe
                20                  25                  30

Gly Gly Pro Gly Met Thr Met His Ser Leu Pro Leu Phe Val Val Lys
            35                  40                  45

Arg Leu Ala Asp Thr Cys Val Pro Gly Gly Ala Phe Leu Ile Ala Leu
        50                  55                  60

Leu Cys Ser Leu Ser Ser Thr Ala Met Ala Ala Gly Pro Ser Asp Trp
65                  70                  75                  80

Met Arg Gly Asp Pro Asn Glu Thr Leu Leu Arg Gln Thr Asp Lys Gln
                85                  90                  95

Ile Glu Lys Val Asn Glu Glu Leu Arg Asn Val Thr Ser Gln Ala Val
                100                 105                 110

Glu Lys Ala Gln Gln Phe Gln Leu Asn Leu Pro Gly Thr Ser Glu Glu
            115                 120                 125

Gln Thr His Thr Ile Arg Ser Ile Leu Glu His Asp Leu Asp Gly Ile
        130                 135                 140

Ala Leu Asn Gln Arg Leu Arg Arg Ile Arg Arg Trp Val Asn Ser Gly
```

```
                 145                 150                 155                 160
        Glu Ile Glu Asn Pro Glu Ser Leu Phe Trp Leu Gln Ile Ile Asp Gln
                         165                 170                 175

Phe Ser Lys Trp Phe Pro
                    180

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
atgatgagat tagttcaac g                                                  21

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4
tcatgggaac cacttgctg                                                    19

<210> SEQ ID NO 5
<211> LENGTH: 234
<212> TYPE: DNA
<213> ORGANISM: Arabidopsis thaliana

<400> SEQUENCE: 5
atggcaatgg ctgttttccg tcgcgaaggg aggcgtctcc tcccttcaat cgccgctcgc       60
ccaatcgctg ctatccgatc tcctctctct tctgaccagg aggaaggact tcttggagtt      120
cgatctatct caactcaagt ggtgcgtaac cgcatgaaga gtgttaagaa catccaaaag      180
atcacaaagg caatgaagat ggttgctgct tccaagctta gagcagttca aggc            234
```